United States Patent
Ozako

(10) Patent No.: US 10,723,882 B2
(45) Date of Patent: Jul. 28, 2020

(54) BLACK ISOINDOLINONE PIGMENT AND COLORING AGENT

(71) Applicant: DAINICHISEIKA COLOR & CHEMICALS MFG. CO., LTD., Tokyo (JP)

(72) Inventor: Shuwa Ozako, Tokyo (JP)

(73) Assignee: DAINICHISEIKA COLOR & CHEMICALS MFG. CO., LTD., Tokyo (JP)

( * ) Notice: Subject to any disclaimer, the term of this patent is extended or adjusted under 35 U.S.C. 154(b) by 0 days.

(21) Appl. No.: 16/474,432

(22) PCT Filed: Dec. 27, 2017

(86) PCT No.: PCT/JP2017/046978
§ 371 (c)(1),
(2) Date: Jun. 27, 2019

(87) PCT Pub. No.: WO2018/131488
PCT Pub. Date: Jul. 19, 2018

(65) Prior Publication Data
US 2019/0338130 A1    Nov. 7, 2019

(30) Foreign Application Priority Data

Jan. 13, 2017  (JP) ................. 2017-003779

(51) Int. Cl.
| | |
|---|---|
| *C07D 209/50* | (2006.01) |
| *C09B 1/16* | (2006.01) |
| *C09B 1/20* | (2006.01) |
| *G02B 5/20* | (2006.01) |
| *C08K 5/00* | (2006.01) |

(52) U.S. Cl.
CPC ............ *C09B 1/206* (2013.01); *C07D 209/50* (2013.01); *C08K 5/0041* (2013.01); *C09B 1/16* (2013.01); *C09B 1/20* (2013.01); *G02B 5/20* (2013.01)

(58) Field of Classification Search
CPC ........... C07D 209/50; C09B 1/16; C09B 1/20; C09B 1/206; C08K 5/0041; G02B 5/20
See application file for complete search history.

(56) References Cited

U.S. PATENT DOCUMENTS

| | | | |
|---|---|---|---|
| 2,973,358 A | 2/1961 | Pugin et al. | |
| 3,867,404 A | 2/1975 | von der Crone et al. | |
| 4,865,650 A | 9/1989 | von der Crone et al. | |

FOREIGN PATENT DOCUMENTS

| | | | |
|---|---|---|---|
| GB | 833548 | * | 4/1960 |
| JP | 57-019145 | | 4/1982 |
| JP | 63-161062 | | 7/1988 |
| JP | 2004-514008 | | 5/2004 |
| JP | 2006-058601 | | 3/2006 |
| JP | 2007-522297 | | 8/2007 |
| WO | 02/38664 | | 5/2002 |

OTHER PUBLICATIONS

Chemical Abstracts Registry No. 122146-82-1, indexed in the Registry file on STN CAS Online Aug. 11, 1989. (Year: 1989 ).*
International Search Report, issued in the corresponding PCT application No. PCT/JP2017/046978, dated Feb. 6, 2018, 5 pages.
Sekiguchi et al., "Synthesis of bisazomethine pigments from 4-nitrophthalimide and diamines", Journal of Industrial Chemistry, Chemical Society of Japan, vol. 74, No. 12, pp. 2510-2515, 1971, with English abstract.
Australian Examination Report, issued in the corresponding Australian patent application No. 2017393056, dated Dec. 2, 2019, 3 paegs (all the references listed in the enclosed Australian Examination Report were previously cited in the IDS filed Jun. 27, 2019 and have been considered.).
First Chinese Office Action, issued in the corresponding Chinese patent application No. 201780082647.5, dated Apr. 27, 2020, 13 pages including machine translation (GB 833548 and STN Registry,m RN: 122146-82-1, ACS cited by the Chinese Examiner were cited by the Examiner in the Office Action of Sep. 19, 2019).

* cited by examiner

Primary Examiner — Luara L Stockton
(74) Attorney, Agent, or Firm — Hamre, Schumann, Mueller & Larson, P.C.

(57) ABSTRACT

Provided is an infrared-reflecting black isoindolinone pigment having a novel skeleton, the black isoindolinone pigment having a high blackness (coloring power) and excellent durability such as heat resistance. The black isoindolinone pigment is represented by the following formula (1), wherein each X independently represents a chlorine atom, a bromine atom, or an alkyl group, and $8 \geq n+m \geq 0$.

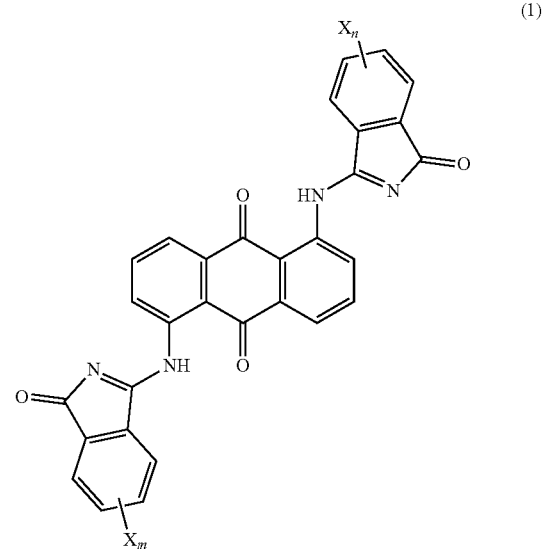

(1)

4 Claims, 3 Drawing Sheets

[Figure 1]
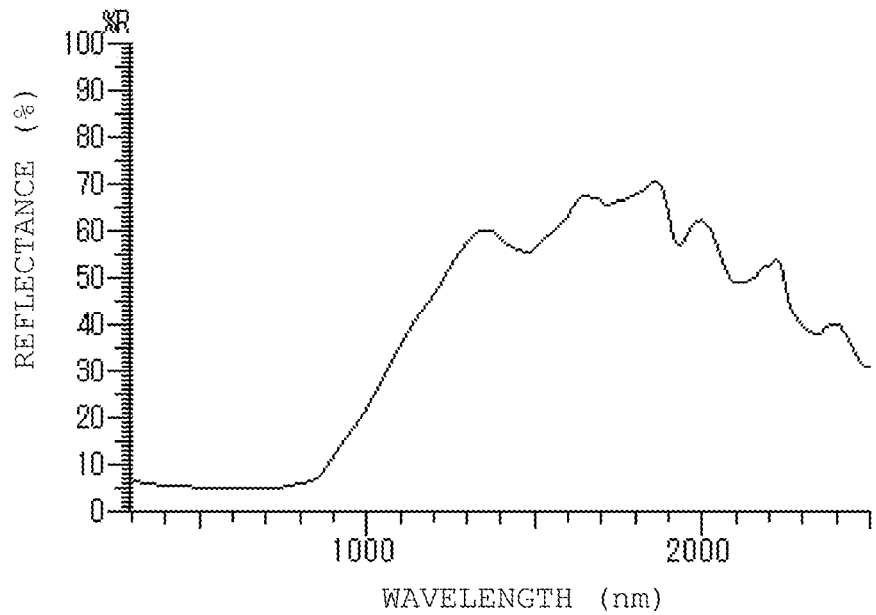
[Figure 2]
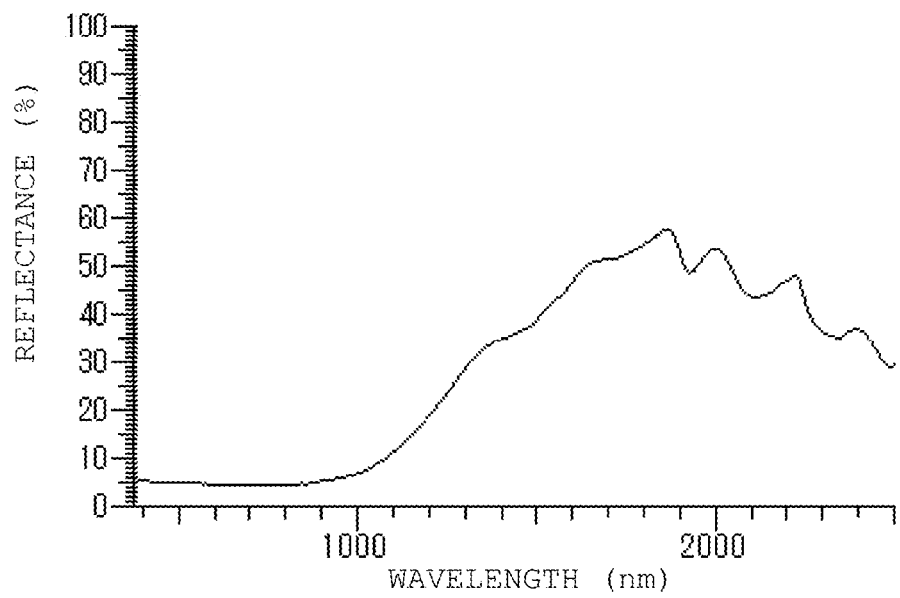

[Figure 3]
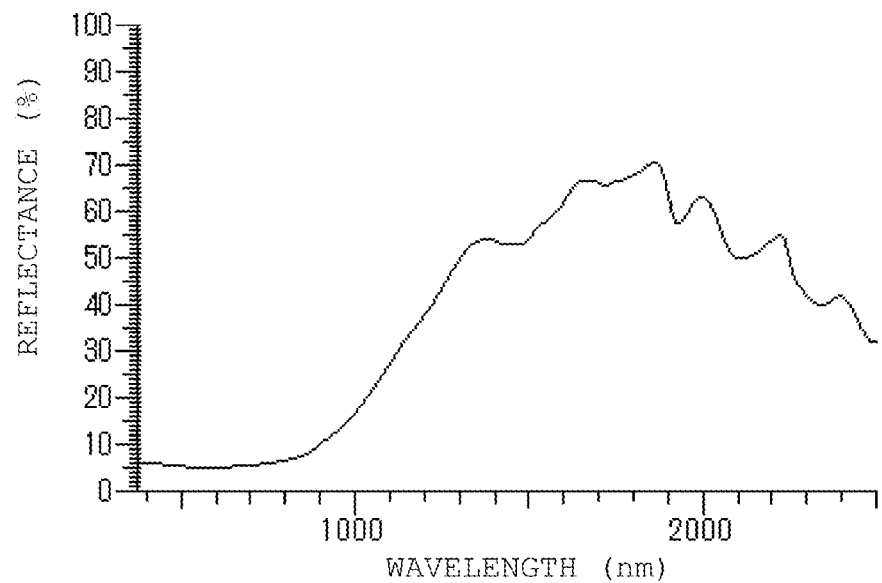
[Figure 4]
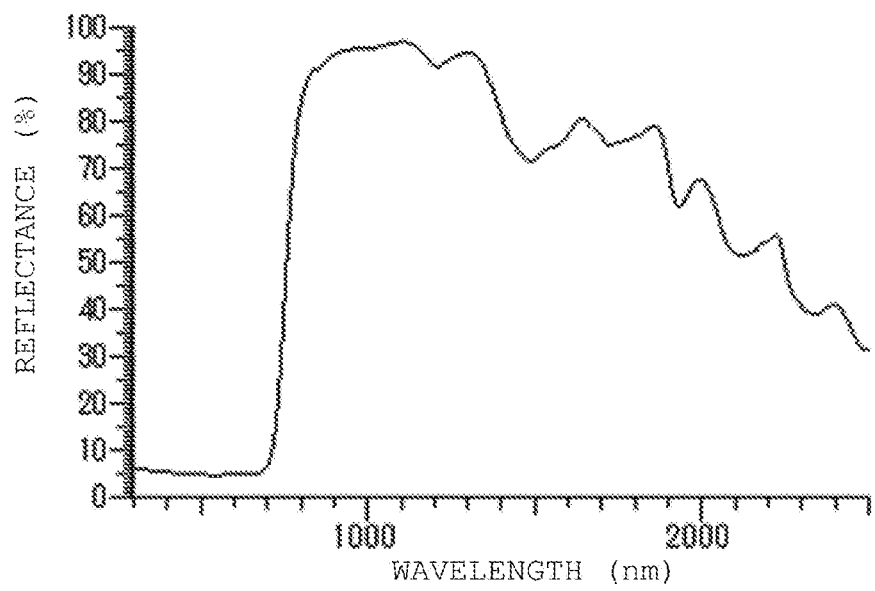

[Figure 5]
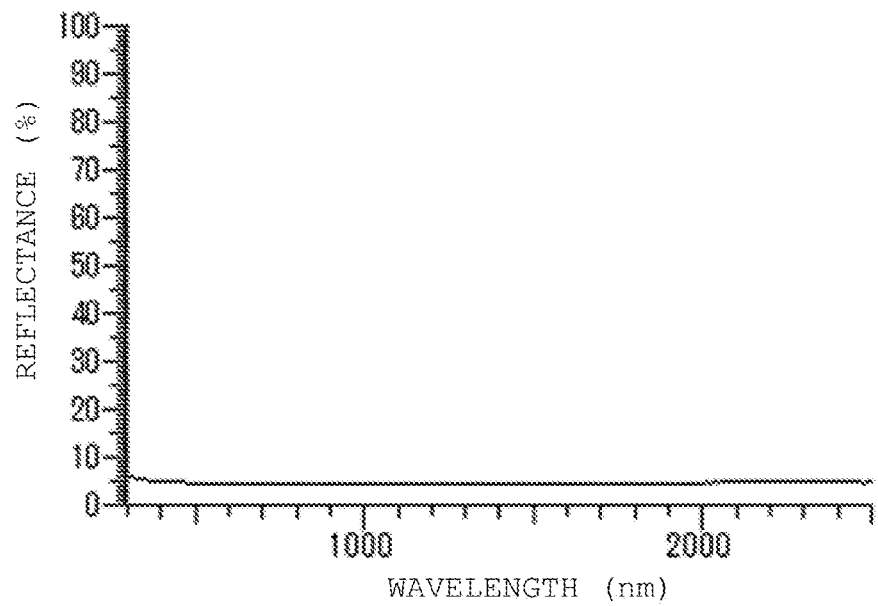

BLACK ISOINDOLINONE PIGMENT AND COLORING AGENT

TECHNICAL FIELD

The present invention relates to a near-infrared non-absorbing black isoindolinone pigment, and a coloring agent using the same.

BACKGROUND ART

Up to now, carbon black-based pigments and iron oxide-based pigments have been general as black pigments that are used as coloring agents for paints, printing inks, and plastics. These black pigments exhibit a black color by absorbing all the rays of light including visible light region of sunlight.

The black pigments (carbon black-based pigments in particular) absorb light in a visible light region (about 380 to about 780 nm) to exhibit a black color, but in fact, also absorb light that is in a near-infrared region including a wavelength region of 800 to 1,400 nm and that greatly contributes to heat. Therefore, there has been a problem that the temperature of articles colored by the black pigments as described above rises easily by being irradiated with sunlight. In addition, as articles colored by a black pigment, sophisticated products such as a black matrix for a color filter have appeared in recent years.

Electric insulation is demanded of a black pigment to be used for constituting a black matrix for a color filter in order to prevent malfunction of a thin film transistor. Carbon black is a pigment having a low electric resistance. Therefore, it cannot be said that carbon black is not appropriate as a coloring material to be used in products such as a black matrix, and it is desirable to use a light-shielding material having a more excellent electric insulation. As related conventional techniques, various electrically insulating black organic pigments whose temperature is unlikely to rise even if they are irradiated with sunlight have been studied (Patent Literature 1). It is to be noted that isoindolinone compounds each having a particular structure, the isoindolinone compounds each being useful as a pigment for coloring a polymer organic material and the like, are proposed (Patent Literatures 2 and 3).

Examples of other uses of a black organic pigment which has attracted attention in recent years include a coloring agent to be used for forming a plastic product for use in laser resin welding. The laser resin welding is a method of welding plastic products without using an adhesive by combining a laser-transmissible resin layer and a laser-absorptive resin layer and performing irradiation with laser of wavelength in a near infrared region (for example, 800 to 1100 nm). Various black organic pigments which are useful as a coloring agent for forming a plastic product for use in laser resin welding have so far been studied.

CITATION LIST

Patent Literature

Patent Literature 1: National Publication of International Patent Application No. 2007-522297
Patent Literature 2: Japanese Patent Laid-Open No. 63-161062
Patent Literature 3: Japanese Patent Publication No. 57-019145

SUMMARY OF INVENTION

Technical Problem

However, each of the isoindolinone compounds proposed in Patent Literatures 2 and 3 is a pigment that exhibits a yellow color, an orange color, or a red-orange color and is therefore unsuitable as a pigment that constitutes a black matrix for a color filter, or the like.

In addition, it cannot be said that carbon black is suitable as a coloring material to be used in a laser-transmissible resin layer. Therefore, a coloring agent having an excellent transparency of light in a near infrared wavelength region and having suitability (dispersibility, blackness) for coloring a plastic product has been desired.

The present invention has been completed in consideration of such problems of the conventional techniques, and an object of the present invention is to provide an infrared-reflecting black isoindolinone pigment having a novel skeleton, the black isoindolinone pigment having a high blackness (coloring power) and excellent durability such as heat resistance. In addition, another object of the present invention is to provide a coloring agent using the above-described black isoindolinone pigment.

Solution to Problem

That is, according to the present invention, a black isoindolinone pigment described below is provided.

[1] A black isoindolinone pigment represented by the following formula (1).

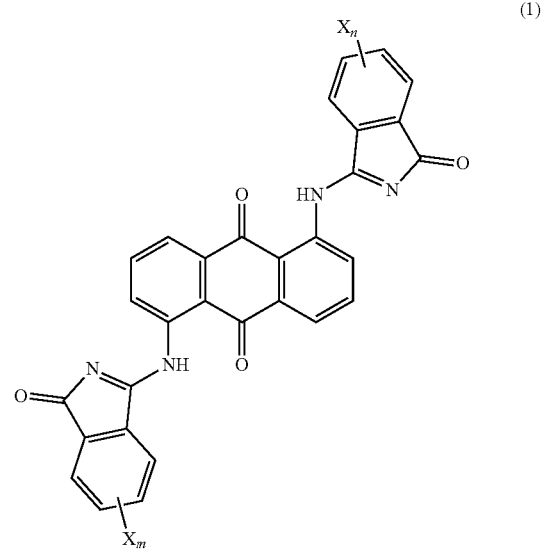

wherein each X independently represents a chlorine atom, a bromine atom, or an alkyl group, and $8 \geq n+m \geq 0$.

[2] The black isoindolinone pigment according to [1], represented by the following formula (1-1), (1-2), or (1-3).

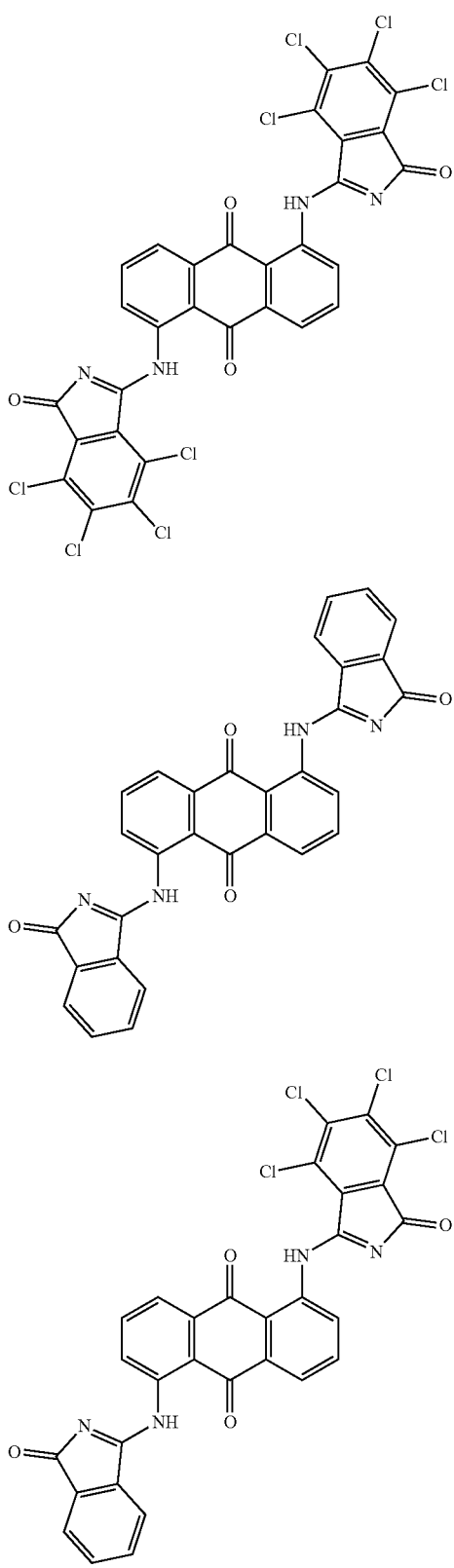

(1-1)

(1-2)

(1-3)

[3] The black isoindolinone pigment according to [1] or [2], having a blackness of 240 or more in an alkyd/melamine baking paint.

Further, according to the present invention, a pigment coloring agent described below is provided.

[4] A coloring agent containing the black isoindolinone pigment according to any one of [1] to [3].

[5] The coloring agent according to [4], to be used for forming a black matrix for a color filter, or a light shielding film.

[6] The coloring agent according to [4], to be used for forming a plastic product for use in laser resin welding.

Advantageous Effects of Invention

According to the present invention, an infrared-reflecting black isoindolinone pigment having a novel skeleton, the black isoindolinone pigment having a high blackness (coloring power) and excellent durability such as heat resistance can be provided. In addition, according to the present invention, a coloring agent using this black isoindolinone pigment can be provided.

BRIEF DESCRIPTION OF DRAWINGS

FIG. 1 is a visible-infrared absorption spectrum of a coating film formed using a pigment (1-1) of Example 1.
FIG. 2 is a visible-infrared absorption spectrum of a coating film formed using a pigment (1-2) of Example 2.
FIG. 3 is a visible-infrared absorption spectrum of a coating film formed using a pigment (1-3) of Example 3.
FIG. 4 is a visible-infrared absorption spectrum of a coating film formed using a pigment (4) of Comparative Example 3.
FIG. 5 is a visible-infrared absorption spectrum of a coating film formed using a pigment (5) of Comparative Example 4.

DESCRIPTION OF EMBODIMENTS

<Black Isoindolinone Pigment>

Hereinafter, embodiments according to the present invention will be described, but the present invention is not limited to the following embodiments. A black isoindolinone pigment according to the present invention is a pigment having a structure represented by the following formula (1). Hereinafter, the details will be described.

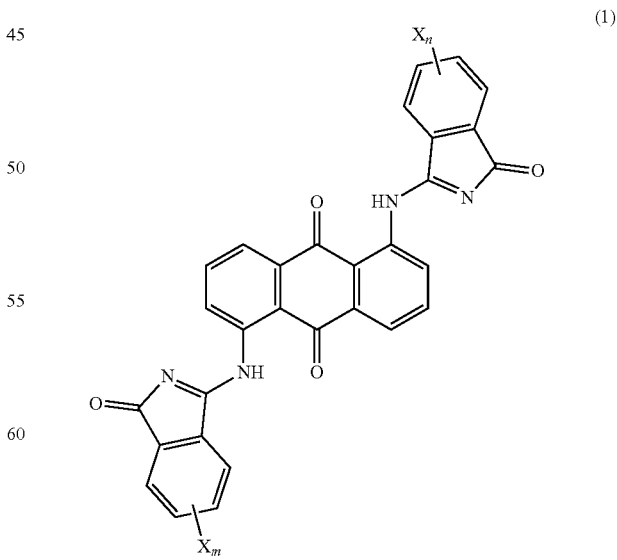

(1)

wherein each of X independently represents a chlorine atom, a bromine atom, or an alkyl group, and 8≥n+m≥0.

In formula (1), the alkyl group represented by X is preferably a lower alkyl group having 1 to 6 carbon atoms and optionally having a branch and is more preferably a lower alkyl group having 1 to 3 carbon atoms.

One of the important characteristics of the black isoindolinone pigment according to the present invention is that it has a structure represented by formula (1). The pigment having a structure represented by formula (1) has pigment properties which are equal to or higher than those of the other isoindolinone pigments. In addition, the black isoindolinone pigment according to the present invention has a 1,5-diaminoanthraquinone skeleton in the structure thereof and therefore exhibits a special color tone.

The color tone of the pigment represented by formula (1) is different from those of the other isoindolinone pigments. A general isoindolinone pigment is a bright-color pigment exhibiting a yellow to orange color. In contrast, the pigment represented by formula (1) effectively absorbs light in a wavelength region of 400 to 850 nm and therefore exhibits an excellent black color.

As a result of diligent studies conducted by the present inventors, it has been made clear that a compound having a 1,5-diaminonaphthalene skeleton, the compound represented by the following formula (2), and a compound having a 2,6-diaminoanthraquinone skeleton, the compound represented by the following formula (3), do not exhibit a black color. It is to be noted that it is inferred that the pigment represented by formula (1) forms an intramolecular hydrogen bond between carbonyl oxygen of anthraquinone and hydrogen of an amino group to have a planar structure. Therefore, it is considered that strong intermolecular n-n interaction is formed and even light in a longer wavelength region is absorbed.

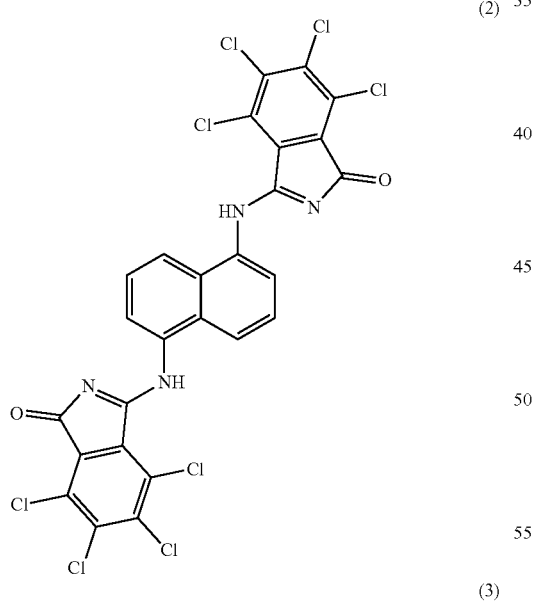

(2)

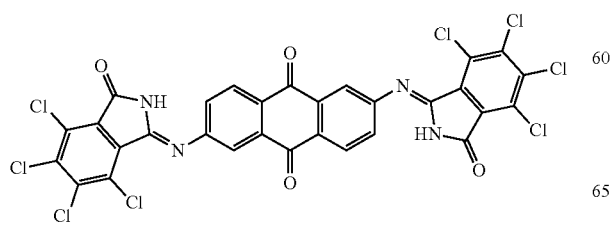

(3)

In addition, the pigment represented by formula (1) exhibits a bluish black color with h*=270 to 290 (L*C*h* color system) in a deep color. Enhancement of design properties has been demanded in various fields in recent years. For example, with respect to a black color, a bluish black with a luxurious feel is demanded. The black isoindolinone pigment according to the present invention is suitable as a black pigment with high jetness.

(Method for Producing Black Isoindolinone Pigment)

The black isoindolinone pigment according to the present invention can be produced, for example, by reacting a compound represented by the following formula (A), a compound represented by the following formula (B), and a compound represented by the following formula (C) in an inert solvent.

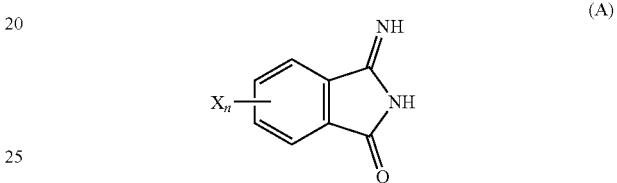

(A)

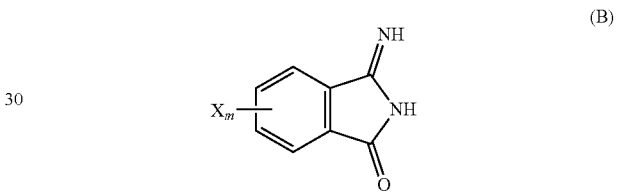

(B)

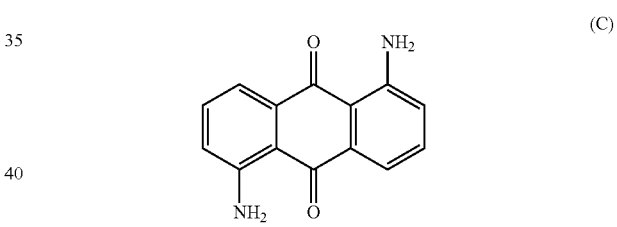

(C)

wherein each of X independently represents a chlorine atom, a bromine atom, or an alkyl group, and 8≥n+m≥0.

Specific examples of 3-iminoisoindolin-1-ones represented by formula (A) and (B) include compounds represented by the following formulas. These compounds can be synthesized from an acid anhydride according to a known method.

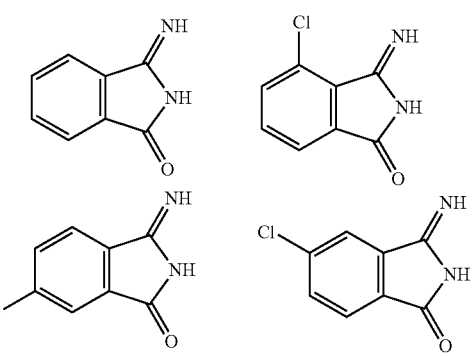

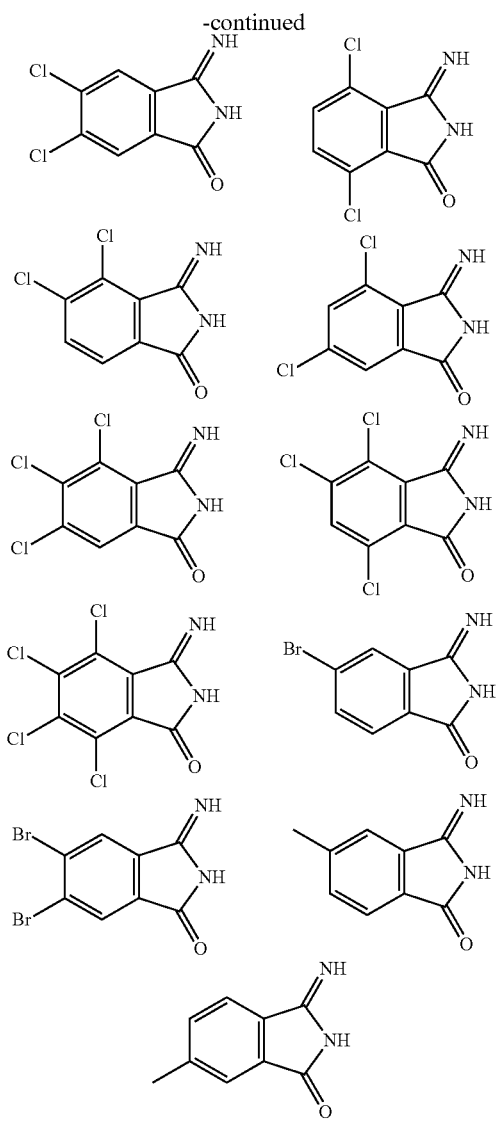

The above-described compounds each having an isoindolinone structure easily undergoes hydrolysis, and therefore a hydrophobic solvent is preferably used as the inert solvent. Specific examples of the hydrophobic solvent include: aliphatic hydrocarbons such as n-hexane, n-heptane, cyclohexane, methylcyclohexane, ethylcyclohexane, and 2-methylpentane; and aromatic hydrocarbons such as toluene, xylene, chlorobenzene, dichlorobenzene, nitrobenzene, and chloronaphthalene. It is to be noted that a solvent having a high dissolving power and a high boiling point, such as chlorobenzene, dichlorobenzene, nitrobenzene, or chloronaphthalene, is preferably used because the reaction progresses smoothly.

The reaction temperature is preferably set to 100 to 140° C. If the reaction is performed at a temperature lower than 100° C., large amounts of mono-substituted products are liable to be produced and the yield of a target compound may be lowered. It is to be noted that co-existence of an acid as a catalyst is preferable because the reaction progresses more smoothly.

Performing a pigmentation treatment in which heating and stirring are performed at 150 to 200° C. in an inert solvent is preferable because the blackness of a resultant pigment increases. Specific examples of the inert solvent include aromatic hydrocarbons such as xylene, dichlorobenzene, nitrobenzene, and chloronaphthalene.

<Coloring Agent>

A coloring agent according to the present invention contains the above-described black isoindolinone pigment. For example, the coloring agent which is a coloring composition can be obtained by allowing the above-described black isoindolinone pigment to be contained (dispersed) in a liquid dispersion medium or a solid dispersion medium. That is, a pigment component containing the black isoindolinone pigment may be dispersed in a liquid dispersion medium to prepare a liquid composition or may be dispersed in a solid dispersion medium to prepare a solid composition according to the object of coloring, the use, the use method, and the like.

As the pigment component to be dispersed in a dispersion medium such as a liquid dispersion medium or a solid dispersion medium, an additional pigment other than the black isoindolinone pigment can be used. That is, in the dispersion medium, only the black isoindolinone pigment may be dispersed as the pigment component or a pigment component containing the black isoindolinone pigment and the additional pigment may be dispersed. As the additional pigment, a chromatic color pigment, a white pigment, an additional black pigment, and an extender pigment can be used. These pigments can be used singly or in a combination of two or more thereof according to the intended color. By dispersing the additional pigment together with the black isoindolinone pigment, coloring agents which enable dark chromatic coloring, achromatic coloring, and black coloring can be obtained.

The content of the black isoindolinone pigment in the coloring agent may appropriately be set according to the use and is not particularly limited. Specifically, the content of the black isoindolinone pigment in the coloring agent may be set to about 1 to about 50% by mass based on the total mass of the coloring agent.

The coloring agent according to the present invention contains the black isoindolinone pigment having a high blackness (coloring power) and excellent durability such as heat resistance. Therefore, the coloring agent according to the present invention is useful as a coloring agent for forming a black matrix for a color filter, or a light-shielding film. Further, the coloring agent according to the present invention is also useful as a coloring agent for forming a plastic product for use in laser resin welding.

EXAMPLES

Hereinafter, the present invention will specifically be described based on Examples, but the present invention is not limited to these Examples. It is to be noted that "parts" and "%" in Examples and Comparative Examples are each on a mass basis unless otherwise noted.

Production of Pigments (Example 1) Production of Black Isoindolinone Pigment (1-1)

To 130 parts of nitrobenzene, 4.8 parts of 1,5-diaminoanthraquinone, 12.5 parts of 3-imino-4,5,6,7-tetrachloroisoindolinone, and 8.4 parts of para-toluenesulfonic acid monohydrate were added, and a resultant mixture was heated at 130° C. for 3 hours. A resultant product was subjected to hot filtration and washing with methanol and water and was then dried at 80° C. to obtain 11.6 parts of a pigment (1-1) represented by the following formula (1-1). Mass analysis by MALDI was performed to detect a peak of 772.

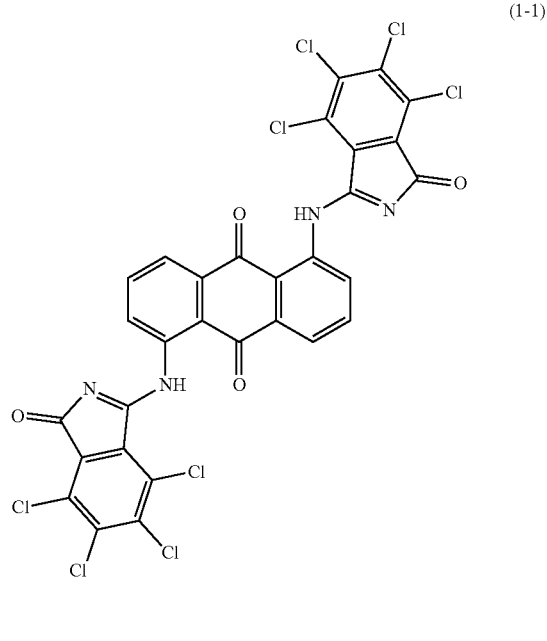 [SMILES: O=C1c2cccc(NC3=NC(=O)c4c(Cl)c(Cl)c(Cl)c(Cl)c43)c2C(=O)c2cccc(NC3=NC(=O)c4c(Cl)c(Cl)c(Cl)c(Cl)c43)c21]

(1-1)

(Example 2) Production of Black Isoindolinone Pigment (1-2)

A pigment (1-2) represented by the following formula (1-2) in an amount of 4.9 parts was obtained in the same manner as in the previously described Example 1 except that 6.1 parts of 3-iminoisoindolinone was used in place of 3-imino-4,5,6,7-tetrachloroisoindolinone. Mass analysis by MALDI was performed to detect a peak of 496.

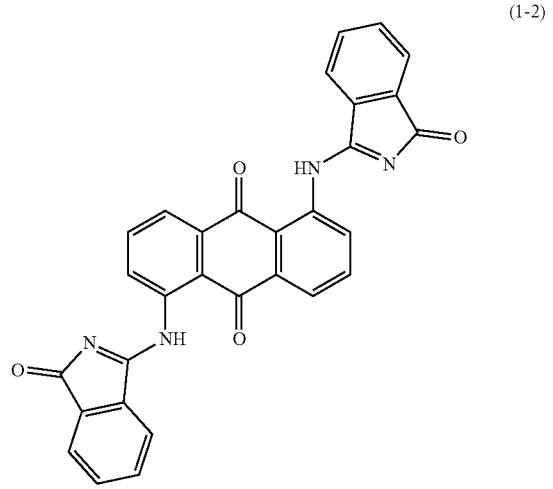 [SMILES: O=C1N=C(Nc2cccc3c2C(=O)c2cccc(NC4=NC(=O)c5ccccc54)c2C3=O)c2ccccc21]

(1-2)

(Example 3) Production of Black Isoindolinone Pigment (1-3)

A mixture of a pigment (1-3) represented by the following formula (1-3), the pigment (1-1) represented by formula (1-1), and the pigment (1-2) represented by formula (1-2) in an amount of 8.6 parts was obtained in the same manner as in the previously described Example 1 except that 6.0 parts of 3-imino-4,5,6,7-tetrachloroisoindolinone and 3.0 parts of 3-iminoisoindolinone were used in place of 3-imino-4,5,6,7-tetrachloroisoindolinone. Mass analysis by MALDI was performed to detect peaks of 496, 634, and 772.

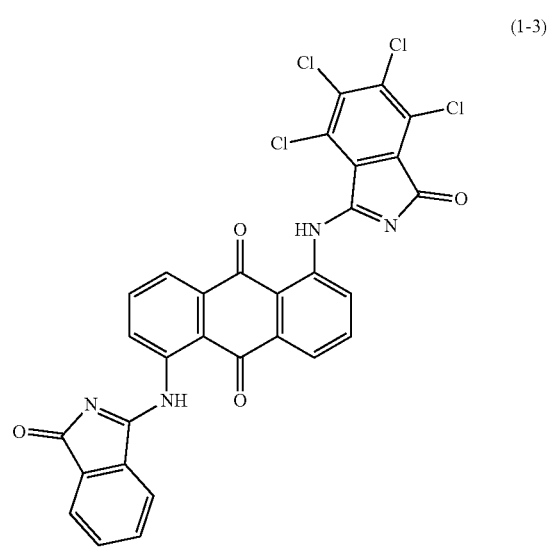 [SMILES: O=C1N=C(Nc2cccc3c2C(=O)c2cccc(NC4=NC(=O)c5c(Cl)c(Cl)c(Cl)c(Cl)c54)c2C3=O)c2ccccc21]

(1-3)

(Comparative Example 1) Production of Orange Isoindolinone Pigment (2)

A pigment (2) represented by the following formula (2) was synthesized referring to the description in Patent Literature 3. The synthesized pigment (2) exhibits an orange color.

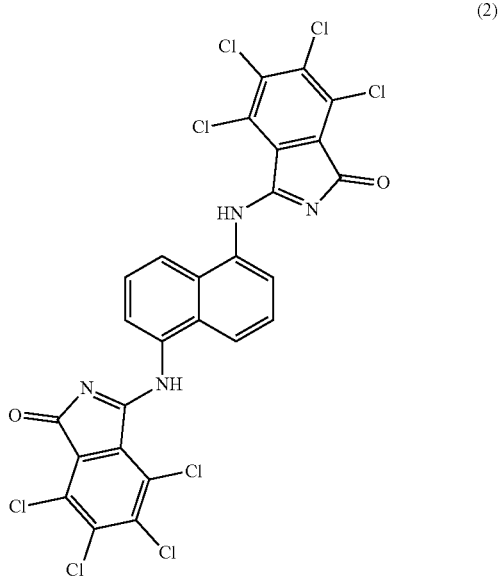 [SMILES: O=C1N=C(Nc2cccc3c(NC4=NC(=O)c5c(Cl)c(Cl)c(Cl)c(Cl)c54)cccc23)c2c(Cl)c(Cl)c(Cl)c(Cl)c21]

(2)

(Comparative Example 2) Production of Orange Isoindolinone Pigment (3)

A pigment (3) represented by the following formula (3) in an amount of 12.2 parts was obtained in the same manner as in the previously described Example 1 except that 2,6-diaminoanthraquinone was used in place of 1,5-diaminoanthraquinone. Mass analysis by MALDI was performed to detect a peak of 772.

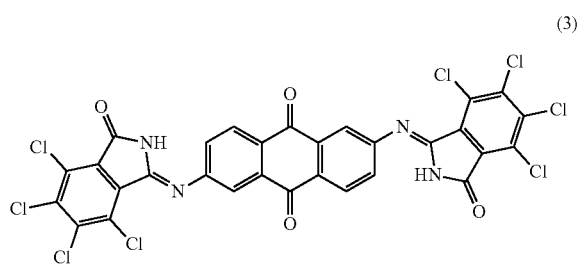 [SMILES: O=C1c2ccc(/N=C3\NC(=O)c4c(Cl)c(Cl)c(Cl)c(Cl)c43)cc2C(=O)c2ccc(/N=C3\NC(=O)c4c(Cl)c(Cl)c(Cl)c(Cl)c43)cc21]

(3)

Comparative Examples 3 and 4

The following commercially available pigments were used as a pigment (4) of Comparative Example 3 and a pigment (5) of Comparative Example 4.
Comparative Example 3 (Pigment (4)): trade name "CHROMOFINE BLACK A1103" (manufactured by Dainichiseika Color & Chemicals Mfg. Co., Ltd.)
Comparative Example 4 (Pigment (5)): trade name "Carbon Black #45B" (manufactured by Mitsubishi Chemical Corporation)
<Evaluation>
(1) Paint Test
Paints (deep color paints) were each prepared by blending respective components according to the combination shown below and dispersing each resultant mixture for 90 minutes using a paint conditioner. Each of the prepared paints was applied on white paper using an applicator (3-mill) and was then baked at 140° C. for 30 minutes, thereby forming a coating film.

Pigment: 1.5 parts
Trade name "Super Beckamine J-820" (*1): 8.5 parts
Trade name "Phthalkyd 133 to 60 (*2): 17.0 parts
Xylene/1-butanol (2/1 (mass ratio)) mixed solvent: 5.0 parts
(*1) Butylated melamine resin (manufactured by DIC Corporation)
(*2) Short oil length alkyd resin of palm oil (manufactured by Hitachi Chemical Company, Ltd.)

(Blackness, Hue Angle, Lightness, and Saturation)
Visible-infrared absorption spectrum of each coating film formed in the previously described "Paint Test" was measured using a spectrophotometer (trade name "U-4100", manufactured by Hitachi High-Technologies Corporation). The measured visible-infrared absorption spectra are shown in FIGS. 1 to 5. The CIE tristimulus values (X, Y, Z) of color were measured according to a conventional method to calculate the blackness, the hue angle, the lightness, and the saturation of each coating film. The results are shown in Table 1.

As shown in FIG. 4, the reflectance of the coating film formed using the pigment (4) of Comparative Example 3 increases rapidly from around 680 nm to the longer wavelength side. However, the rise of the reflectance is too steep to absorb light in a wavelength region of 400 to 700 nm, which is a visible light region, and therefore the blackness is deficient. In addition, as shown in FIG. 5, it can be seen that the coating film formed using the pigment (5) of Comparative Example 4 absorbs light in a wide wavelength region to 2500 nm and does not exhibit infrared reflectivity at all. In contrast, as shown in FIGS. 1 to 3, it can be seen that the coating films formed using the pigments (1-1), (1-2), and (1-3) of Examples 1 to 3 absorb light in a visible light region in a well-balanced manner, thoroughly absorb light in a wavelength region of around 500 to around 800 nm, and therefore exhibit a high blackness. Further, it can also be seen that the coating films formed using the pigments (1-1), (1-2), and (1-3) exhibit a favorable infrared reflectivity.

(Infrared Reflectivity)
The infrared reflectance of each film formed in the previously described "Paint Test" was measured, and the infrared reflectivity was evaluated according to the following evaluation criteria. The results are shown in Table 1.
Good: Infrared reflectance at 1300 nm is 30% or higher
Poor: Infrared reflectance at 1300 nm is lower than 30%
(Heat Resistance)
Thermogravimetry and differential thermal analysis (TG-DTA) were performed for each pigment. The reduced rate at 350° C. was calculated to evaluate the heat resistance according to the following evaluation criteria. The results are shown in Table 1.
Good: Reduced rate at 350° C. is 10% or lower
Poor: Reduced rate at 350° C. is larger than 10%

TABLE 1

| | | | | | Evaluation results (1) | | | |
| | Pigment | Color | Blackness | Hue angle | Lightness | Saturation | Infrared reflectivity | Heat resistance |
| --- | --- | --- | --- | --- | --- | --- | --- | --- |
| Example 1 | (1-1) | Black | 254 | 291 | 2.7 | 3.5 | Good | Good |
| Example 2 | (1-2) | Black | 278 | 34 | 1.4 | 0.5 | Good | Good |
| Example 3 | (1-3) | Black | 246 | 319 | 3.1 | 2.7 | Good | Good |
| Comparative Example 3 | (4) | Black | 223 | 27 | 4.1 | 2.8 | Good | Poor |
| Comparative Example 4 | (6) | Black | 236 | 291 | 3.0 | 0.3 | Poor | Good |

(2) Plastic Coloring Test
Molded plates (plates each having a portion with a thickness of 1 mm and a portion with a thickness of 2 mm) were each prepared by blending respective components according to the following combination and performing injection molding using an injection molding machine (manufactured by NISSEI PLASTIC INDUSTRIAL CO., LTD.).

Pigment: 8 parts

Trade name "SUMIPEX LG" (*1) 800 parts

Trade name "Magnesium Stearate": 2 parts (*1) PMMA resin (manufactured by SUMITOMO CHEMICAL COMPANY, LIMITED)

(Color (Blackness))

The color (blackness) of each prepared molded plate was checked visually. The results are shown in Table 2.

(Dispersibility)

Each molded plate was hot-pressed to obtain a thin piece (thickness of 100 μm). The obtained thin piece was observed with a microscope (manufactured by KEYENCE CORPORATION) to evaluate the dispersibility according to the following evaluation criteria. The results are shown in Table 2.

Good: Pigment particles are not observed

Poor: Pigment particles are observed (Laser Weldability)

As a laser-absorptive resin layer, a resin molded plate (thickness of 1 mm) containing carbon black was prepared. The previously described molded plate (thickness of 1 mm) was used as a laser-transmissible resin layer, and these two pieces of plates were laminated, and pinched and fixed by a clip. The two pieces of plates were welded using a laser apparatus (trade name "LP-Z", manufactured by Panasonic Corporation, 3D-Control FAYb Laser Marker). The welded plates were observed, and the laser weldability was evaluated according to the following evaluation criteria. The results are shown in Table 2.

Good: Even if the clip is removed to lift the plates, the plates are welded.

Poor: When the clip is removed to lift the plates, the plates are separated into two pieces of plates.

TABLE 2

Evaluation results (2)

| | Pigment | Color (blackness) | Dispersibility | Laser weldabilty |
|---|---|---|---|---|
| Example 1 | (1-1) | Bluish black | Good | Good |
| Example 2 | (1-2) | Bluish black | Good | Good |
| Example 3 | (1-3) | Bluish black | Good | Good |
| Comparative Example 1 | (4) | Reddish black | Poor | Good |

INDUSTRIAL APPLICABILITY

The black isoindolinone pigment according to the present invention is useful for uses, such as a black matrix, where a high blackness is demanded. In addition, the black isoindolinone pigment according to the present invention has a high light reflectance in a near infrared region and therefore is useful as a heat ray-reflecting black pigment, the use of which is unsuitable for pigments such as carbon black.

The invention claimed is:

1. A black matrix for a color filter, wherein the black matrix comprises a black isoindolinone pigment represented by following formula (1-2) or (1-3):

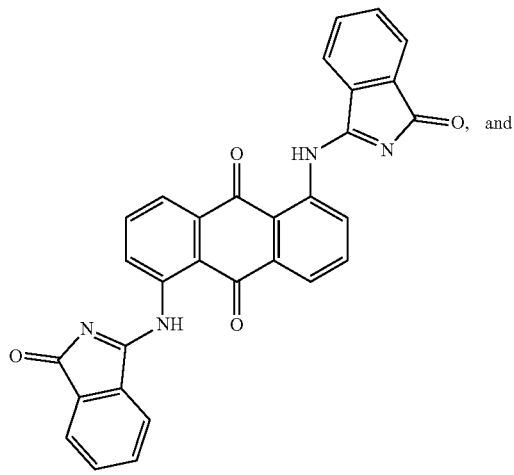

(1-2)

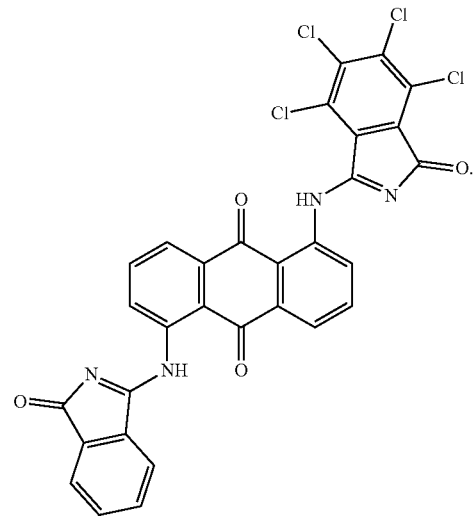

(1-3)

2. A light shielding film comprising a black isoindolinone pigment represented by following formula (1-2) or (1-3):

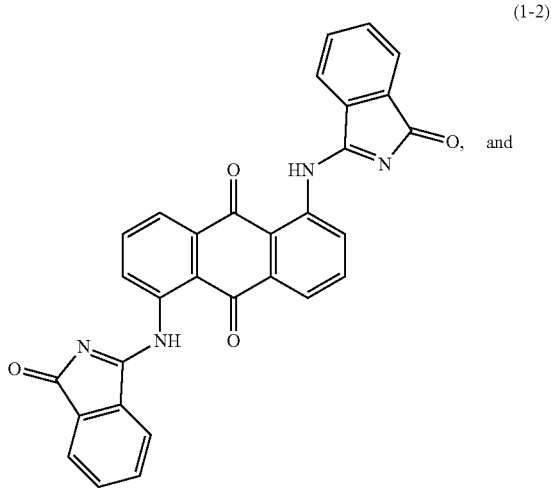

(1-2)

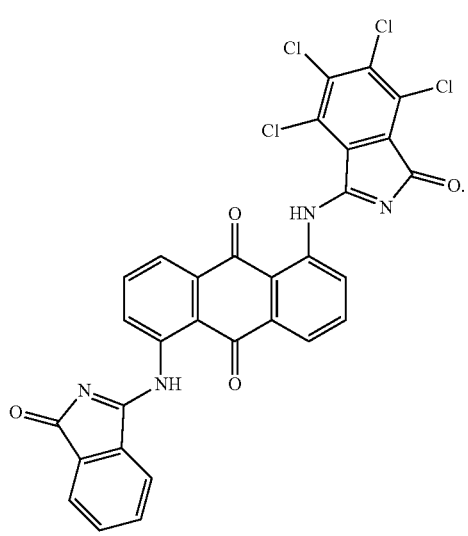
(1-3)
3. A plastic product for use in laser resin welding, wherein the plastic product comprises a black isoindolinone pigment represented by following formula (1-2) or (1-3):
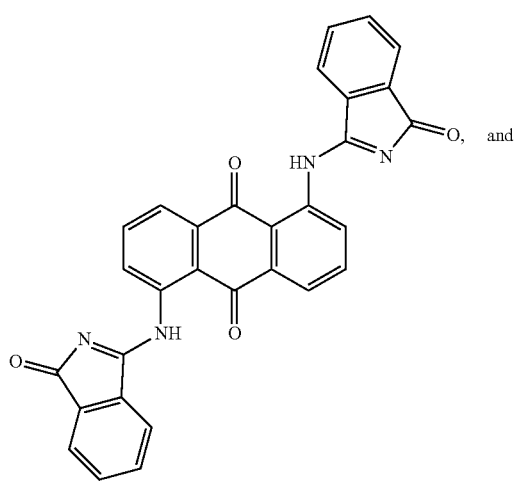
(1-2)
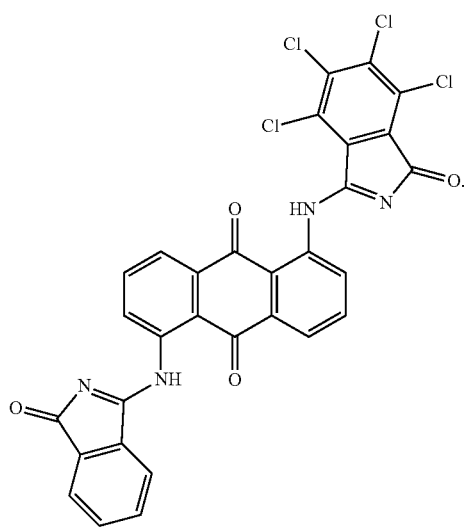
(1-3)
4. A color filter comprising a black matrix,
wherein the black matrix comprises a black isoindolinone pigment represented by following formula (1-2) or (1-3):
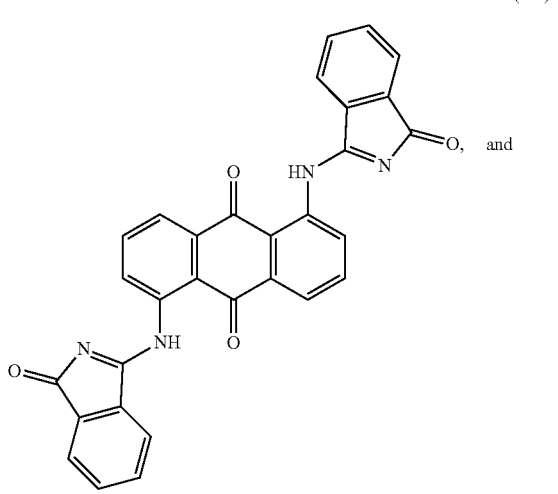
(1-2)
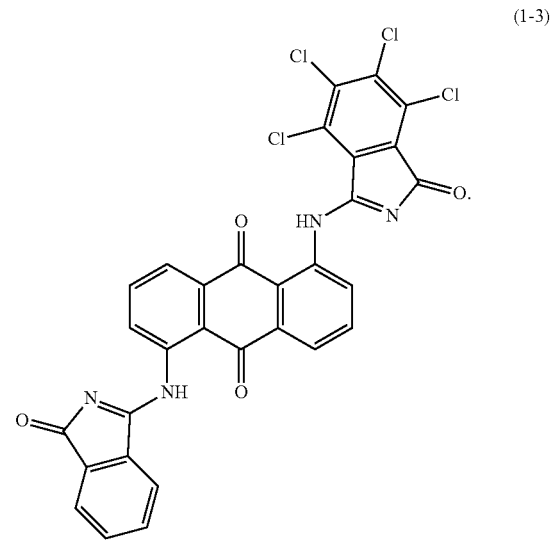
(1-3)
* * * * *